United States Patent
Kensy et al.

(10) Patent No.: US 8,828,337 B2
(45) Date of Patent: Sep. 9, 2014

(54) MICROREACTOR

(75) Inventors: Frank Kensy, Aachen (DE); Carsten Mueller, Herzogenrath (DE); Jochen Buechs, Aachen (DE); Matthias Funke, Aachen (DE)

(73) Assignee: m2p-labs GmbH, Baesweiler (DE)

( * ) Notice: Subject to any disclaimer, the term of this patent is extended or adjusted under 35 U.S.C. 154(b) by 256 days.

(21) Appl. No.: 12/734,054

(22) PCT Filed: Oct. 8, 2008

(86) PCT No.: PCT/DE2008/001623
§ 371 (c)(1), (2), (4) Date: Apr. 19, 2010

(87) PCT Pub. No.: WO2009/046697
PCT Pub. Date: Apr. 16, 2009

(65) Prior Publication Data
US 2010/0248995 A1    Sep. 30, 2010

(30) Foreign Application Priority Data

Oct. 8, 2007 (DE) .......... 10 2007 048 201
Feb. 8, 2008 (DE) .......... 10 2008 008 256

(51) Int. Cl.
| | |
|---|---|
| B01J 8/00 | (2006.01) |
| B01L 3/00 | (2006.01) |
| B01F 11/00 | (2006.01) |
| C12M 1/00 | (2006.01) |
| B01F 15/00 | (2006.01) |
| C12M 1/04 | (2006.01) |
| C12M 1/32 | (2006.01) |

(52) U.S. Cl.
CPC ........ *C12M 23/38* (2013.01); *B01L 2300/0858* (2013.01); *B01L 3/5085* (2013.01); *B01J 2219/00315* (2013.01); *B01F 11/0014* (2013.01); *B01J 2219/00479* (2013.01); *B01F 15/00876* (2013.01); *C12M 23/24* (2013.01); *C12M 23/12* (2013.01); *B01L 2300/0829* (2013.01)
USPC ........... 422/603; 422/553; 422/552; 422/501

(58) Field of Classification Search
USPC ................. 422/553, 552, 503, 603
See application file for complete search history.

(56) References Cited

U.S. PATENT DOCUMENTS

| 5,225,164 A | 7/1993 | Astle |
| 5,792,654 A | 8/1998 | Bohannon et al. |

(Continued)

FOREIGN PATENT DOCUMENTS

| DE | 201 21 739 | 8/2003 |
| EP | 1 733 793 | 12/2006 |

(Continued)

OTHER PUBLICATIONS

Hermann, R., Lehmann, M., Büchs, J., "Characterization of Gas-Liquid Mass Transfer Phenomena in Microtiter Plates," Biotechnol Bioeng, vol. 81, No. 2, Jan. 2003, pp. 178-186. (Spec, p. 2).

(Continued)

*Primary Examiner* — Natalia Levkovich
(74) *Attorney, Agent, or Firm* — Collard & Roe, P.C.

(57) ABSTRACT

A microreactor with at least one cavity, which comprises a bottom, a side wall and an opening disposed opposite the bottom, has a cross-section intersecting the side wall parallel to the bottom, the cross-section having a shape diverging from a round, square or rectangular shape.

24 Claims, 15 Drawing Sheets

(56) References Cited

U.S. PATENT DOCUMENTS

| | | |
|---|---|---|
| 6,896,848 B1 | 5/2005 | Warhurst et al. |
| 2002/0195448 A1* | 12/2002 | Mathus et al. ............... 220/23.4 |
| 2004/0029259 A1* | 2/2004 | McDevitt et al. .......... 435/287.2 |
| 2007/0256510 A1 | 11/2007 | Buchs et al. |
| 2010/0203621 A1 | 8/2010 | Takahashi et al. |

FOREIGN PATENT DOCUMENTS

| | | |
|---|---|---|
| EP | 1 944 080 | 7/2008 |
| JP | 2003-344433 | 3/2003 |
| WO | WO 98/45406 | 10/1998 |
| WO | WO 02/081075 | 10/2002 |
| WO | WO 02/102965 | 12/2002 |
| WO | WO 2005/098397 | 10/2005 |
| WO | 2009/013869 A1 | 1/2009 |

OTHER PUBLICATIONS

Büchs J., "Introduction to advantages and problems of shaken cultures," Biochemical Engineering Journal 7, 2001, pp. 91-98. (Spec, p. 4).

Kensy, F., John, G. T., Hofmann, B., Büchs, J., "Characterisation of operation conditions and online monitoring of physiological culture parameters in shaken 24-well microtiter plates," Bioprocess and Biosystems Engineering, 2005, 75, pp. 75-81. (Spec, p. 4).

International Search Report for PCT/DE2008/001623 dated Jun. 4, 2009.

English Translation of International Preliminary Report on Patentability for PCT/DE2008/001623 dated Jun. 15, 2010 and Written Opinion of International Searching Authority for PCT/DE2008/001623.

* cited by examiner

MICROREACTOR

CROSS REFERENCE TO RELATED APPLICATIONS

This application is the National Stage of PCT/DE2008/001623 filed on Oct. 8, 2008, which claims priority under 35 U.S.C. §119 of German Application No. 10 2007 048 201.0 filed on Oct. 8, 2007 and German Application No. 10 2008 008 256.2 filed Feb. 8, 2008. The international application under PCT article 21(2) was not published in English.

The invention relates to a microreactor with at least one cavity, which comprises a bottom, a side wall and an opening disposed opposite the bottom.

6, 24, 48, 96, 384 or more individual microreactors, for example, can be produced by means of conventional microreactor arrays (so-called microtitre plates). Just as the number of microreactors can be greatly varied, the volume of the individual reactors can also vary. Whilst mention is already be made of microreactors on scales of less than 10 ml, a further reduction in the volume to less than 1 ml, less than 500 µl, less than 100 µl or even less than 10 µl can take place.

A microreactor serves as a reaction vessel for biochemical, chemical or enzymatic reactions as well as microbial fermentations. A reactor array permits the investigation of cell cultures with a high degree of parallelism with a small working volume, high data acquisition and the possibility of simplified automation. Such arrays are particularly well suited for the automation of screening tests under improved mixing and mass transfer conditions and they enable an operation which is isolated or sterile, aseptic or monoseptic to the exterior.

The screening of biological systems is necessary in many areas of biology, chemistry, chemical engineering, pharmaceuticals and medicine (e.g. the selection of suitable biological strains, enzymes or suitable culture media and culture conditions). There is a need here for high sample throughput rates (parallelisation of tests) and for a reduction in the sometimes expensive starting materials.

This need cannot be met with the bioreactors used today, such as shaking flasks, small fermenters and test tubes. The established techniques do not meet the need for automation, cost minimisation and the required high throughput. The need for many parallel tests on the microliter scale exists precisely with biocatalytic systems, since such processes generally proceed more slowly and, precisely in the development phase, are more expensive than comparable chemical processes. The need therefore exists to develop microbioreactors which deliver, in the smallest possible space, a suitable environment for biological cultivation and for biocatalytic reactions.

Two criteria should be highlighted as important prerequisites for suitable operating conditions here: the possibility of carrying out the appropriate tests under sterile and monospetic conditions and the guarantee of a mass transfer (liquid-liquid, liquid-gas, solid-liquid, solid-gas) that is suitable and sufficient for the biological culture or the biocatalytic reaction system.

Microreactor arrays, such as for example microtitre plates, offer an ideal platform for achieving a high degree of parallelisation. On account of the small reaction volumes (e.g. >10 µl to <10 ml per chamber), the high degree of parallelisation (e.g. 6 to 1536 chambers per plate) and the possibility of automating the cultivation processes (form manipulatable by robots), microreactor arrays represent overall the most cost-effective and promising bioreactor.

Furthermore, the use of non-invasive, optical measuring methods for acquiring process variables in this type of reactor is already well advanced. In addition, the operating conditions in shaken microtitre plates with respect to mass transfer (maximum oxygen transfer capacity, OTRmax) are already well characterised.

It has been able to be shown that, with standard 96-well microtitre plates (round cross-section), it is only possible to achieve maximum oxygen transfer rates OTRmax of 0.030 mol/l/h with air gassing. (Hermann R., Lehmann M., Büchs J.: Characterization of gas-liquid mass transfer phenomena in microtitre plates. Biotechnol Bioeng, 81(2), 178-186, 2003). This is however very often not sufficient for the culture management of aerobic, microbial cultures in order not to manage the culture in a oxygen-limited manner.

The requirements of many microbial cultures often lie above OTR values of 0.05 mol/l/h, and in many cases they even reach OTR values of 0.1 mol/l/h in batch processes and even up to 0.3 mol/l/h in feed-batch processes. Higher OTRmax values of 0.1-0.15 have been able to be reached in square and round 96 deep-well plates. However, these values were only able to be reached with correspondingly small filling volumes of 200 µl. The liquid is thereby almost completely removed from the bottom and an optical measurement at the bottom is no longer possible. In addition, there are at present no deep-well plates with an optically transparent bottom, and this therefore makes an optical measurement through the bottom impossible.

Microtitre plates are already used at present for the screening of biological systems. For this purpose, the individual reaction chambers are filled, inoculated and incubated on a rotary shaker. As a result of the usually orbital shaking motion, the input of oxygen into the reaction liquids is improved and thorough mixing of the reaction mixture is achieved. In order to keep the system sterile, the microtitre plates are covered by an air-permeable membrane (pore size<0.2 µm) or an airtight film or a cover construction or are cultivated open in a sterile environment.

The microtitre plates used for the described applications are nowadays offered in two basic designs by a very wide variety of manufacturers: With circular or with rectangular cavities. The first microtitre plates were produced in 1951 by the Hungarian Dr. G. Takatsky and had a round cross-section. Microtitre plates with a square and rectangular cross-section were then introduced in the 90s. Microtitre plates are used however in very many spheres of chemistry, medicine, biotechnology and biology, so that virtually no development especially for the cultivation of cells has taken place.

Some of the few exceptions are described in patent specification U.S. Pat. No. 5,225,164 from the year 1991, in which the possibility is described of providing a flow disruptor projecting into the cavity in a square cavity on at least one of the vertical walls of the cavity. The solution can in principle lead to improved mass transfer, but the flow breakers, if they have a pronounced definition, can severely restrict circulation of the liquid in the reactors, good mixing and good mass transfer.

On the other hand, flow breakers can contribute towards considerable drop formation/splashes, and this leads to inhomogeneities, increased wall growth and to the wetting and blockage of the gas-permeable cover of the plates (Büchs J., Introduction to advantages and problems of shaken cultures, Biochem. Eng. J. 7(2), 91-98, 2001). Furthermore, it is not possible to find on the market or in the specialist literature any further indication of the implementation and investigation of a microtitre plate with a variation of the cavity geometry (apart from the circular and the rectangular cross-section).

It is known from practice that the use of microtitre plates with circular cavities in a measuring system such as the BioLector technology (WO 2005/098397) marketed by the firm m2p-labs leads to problems with measurement value acquisition during the shaking process. The permanent shaking motion is necessary in order to guarantee a continuous good mass transfer into the reaction liquid, but with high shaker speeds it leads to a drastic reduction of the liquid layer up to running completely dry at the bottom of the cavity occupied by sensors and thus to problems with measurement value acquisition (see also: Kensy F., John G. T., Hofmann B., Büchs J., Characterisation of operation conditions and online monitoring of physiological culture parameters in shaken 24-well microtiter plates; Bioprocess and Biosystems Engineering 28(2), 75-81, 2005).

There are various systems on the market for covering such microtitre plates. In the first place, most manufacturers of microtitre plates also supply a plastic cover, which is placed loosely onto the microtitre plate.

In the second place, the concept of a glued-on film or membrane has become established on the market. Additional devices (sealers) for manual or automated operation can also be obtained from various suppliers for this use.

As a third variant, mats of flexible plastic (e.g.: silicon) are marketed, the nap-like protruberances whereof engage in each individual cavity and thereby close the latter.

Only two systems are known on the market which press a dimensionally stable cover tightly onto the microtitre plate by force. In the first place, there is a system which is marketed as the "Sandwich Cover Plate" by the firm EnzyScreen.

In the second place, a cover is known from patent specification U.S. Pat. No. 6,896,848, which completely engages around the microtitre plate and thus gains a grip on the microtitre plate. Special devices for the application or placement of the cover are required for both systems. Both systems cannot therefore be automated without additional holding devices or applicators.

The reaction vessels known and described according to the prior art are not suitable for the majority of applications (in particular chemical reactions with a gas phase or cell cultivations). They have the following drawbacks:
  insufficient gas exchange between the surrounding gas phase and the liquid phase in the cavity
  insufficient or excessively slow mixing of various constituents inside the cavity (liquid-liquid mixture or solid-liquid suspension)
  with increasing shaking frequency, the liquid rises up at the wall and already reaches the upper edge of the cavity at relatively low shaking frequencies. The usable filling volume is thus limited, because otherwise the escape of the liquid over the edge of the cavity or clogging of the applied covering membrane would occur.
  running dry at the bottom of the cavity at raised speeds, which does not permit a measurement with sensors immobilised or fixed at the bottom or optical measurements in the liquid from beneath the bottom.
  the use of, for example, square cavity cross-sections or cavities with flow disruptors can lead to flow disruptions which give rise to the formation of drops and/or aerosols. This can lead to the deposition of solids and reaction components at the walls of the cavity and to clogging of the microreactor array covering. Optical measurements can also be adversely affected by the formation of drops and/or aerosols.
  foam formation with excessively prominent flow disruptors.

With regard to the various systems of microreactor array coverings that are currently known, the following drawbacks in particular are to be regarded as serious:

no firm and tight closure of the microtitre plate, especially during a shaking motion (only standard cover made of plastic to be placed on loosely).
  complicated manipulations, in some cases accessories are necessary in order to fix a covering on the microtitre plate. No or only elaborate possibilities and expensive solutions for automation (adhesive films and plastic mats).
  no or only insufficient/inhomogeneous gas supply and/or undesirably high evaporation of reaction liquid when use is made of established microtitre plate coverings (films, cover systems).
  no possibility of sampling or liquid/solid addition/removal into or from the microtitre plate without the risk of contamination for the reaction being carried out, since no covering exists which can be closed again without additional expenditure or without additional devices and at the same time guarantees a gas transfer.

The problem of the invention is to overcome the drawbacks of conventional microtitre plates described above and thus to extend the established concept of a microtitre plate as a vessel predominantly for chemical and biochemical reaction set-ups basically to the creation of a fully adequate and universally applicable reaction and cultivation system, in that the following points are preferably complied with.

With regard to microreactor arrays, they are:
  intensified gas exchange with the liquid inside a cavity
  intensification of the mixing of a liquid or suspension in a cavity
  prevention of spilling over of the reaction solution from the reaction vessels at the required high shaking speeds.
  prevention of the bottom of a cavity running dry during the shaking process (e.g.: in order to guarantee an optical or any measurement at the bottom or through the bottom) and creation of a constant contact with sensors possibly fitted at the bottom of the cavity.
  prevention of drop and/or aerosol formations, which can adversely affect the measurements, deposit reaction constituents and/or biomasses at the walls and/or may hinder or block, due to clogging, the mass transfer through the gas-permeable cover of the microreactor array.
  low foam formation due to liquid motion as homogeneous as possible.

With regard to the cover of the microreactor arrays, they are:
  firm and tight closure of each individual cavity with respect to the adjacent cavities and the surroundings by application of a cover, which can be locked on the microreactor array and/or released again.
  straightforward handling of the cover with the possibility of automation with conventional gripping arms of, for example, liquid handling systems
  reduction of evaporation with at the same time sufficient gas transfer through openings in the cover, by adapting the size of these openings and/or by the use of diffusion-controlling materials with which these openings are covered.
  possibility of sterile sampling and/or supply and removal of liquids or solids into or out of the individual cavities of a microreactor array.

With regard to a microreactor, the problem is solved in that a cross-section intersecting the side wall parallel to the bottom has a shape diverging from a round, square or rectangular shape. Shape is understood here to mean the basic shape, this basic shape not being changed by smaller flow breakers.

The solution to the described problems takes place by changing the geometry of a cavity, away from the established geometries of a circular cylindrical shape or a rectangular cross-section.

The problem is solved in that the round or square cavities known according to the prior art are changed in such a way that the positive properties of a flow disruption by the introduction of protrusions or indentations in the cavity and the positive properties of a round cavity and thus as undisrupted a flow as possible supplement one another in an ideal manner for the described case of application.

As a result of the new proposed shapes of the cavities, the rotational liquid motion is moderately disrupted by the application of an orbital shaking motion.

As a result of the disruption or hindering of the uniform wall flow, a turbulent flow profile is formed which has a positive effect on the mixing and the mass transfer out of the gas phase into the liquid phase and vice versa. The formation of protrusions and indentations should be coordinated in such a way that drop and aerosol formation does not occur, which can lead to clogging of a placed-on cover (e.g. a membrane) or the collection or deposition of liquid or solid (e.g. biomasses) at the reactor walls. The effect of coordinating the flow-disrupting action is also that the liquid continuously wets the bottom and optical or other measurements at the cavity bottom are thus enabled. As a result of coordinating the flow-disrupting action, the possible filling volume can also be increased until spilling over of the liquid occurs at a corresponding shaking frequency.

The problem can be solved by the creation of different cavity geometries:

The first approach at a variation for the base area of the cavities proceeds from one extreme of a square base area and, by increasing the number of corners, approaches the other extreme of a round base area. It is therefore proposed that the cross-section should comprise more than four corners.

The construction-relevant length of the base side of a polygon can also be calculated, with a given area of $112.16\ mm^2$, by the construction of a triangle between a base side and two adjacent radii of the polygon. It is therefore alternatively proposed that the cross-section should comprise less than four corners.

In the second approach at a variation, again proceeding from a square, the transition to the circular base area was achieved by the construction of circles with increasing radius in the corners of the square. The magnitudes of the radius of the corner circle, as well as the remaining straight line of the initial square, are of relevance for the construction.

It is advantageous if the cavity diverges from the shape of a polygon.

The shape can be described by the fact that a cross-section intersecting the side wall parallel to the bottom comprises at least one concave and/or convex segment of a circle, which projects with a radius into the cross-section or out of the latter, this radius amounting to between 0.067 and 0.49 times the diagonal of the cross-section.

One example makes provision such that the basic shape of the cross-section is an arbitrary polygon or a circle which comprises a plurality of concave or convex segments of a circle.

The cross-section can comprise an arc which forms a segment of a circle of more than 90°, or the cross-section can comprise more than 3, preferably more than 4 arcs, which form in each case a segment of a circle of more than 90°.

In the third approach at a variation, a pentagon was selected as the initial shape and transformed gradually into a circle by rounding off the corners.

With regard to the second and the third approach at a variation, it has proved to be advantageous if the cross-section comprises corners with a radius of more than 0.5 mm.

A fourth approach at modifying the originally circular basic shape of the cavity consists in introducing flow disruptors of differing shape and size. The base area arising here cannot in many cases be readily calculated. In order to meet the stipulation here of $112.16\ mm^2$, the area was measured after drawing with the software AutoCAD, Ver. 14.01 of the firm Autodesk Inc. and then scaled accordingly.

A shape thus arises with which the cross-section comprises a region projecting into the cavity. An alternative makes provision such that the cross-section comprises a region projecting out of the cavity. It is advantageous for many embodiments if the region is disposed in a corner.

Furthermore, it is proposed that a plurality of such regions be provided with different dimensions or that a plurality of such regions lie adjacent to one another.

In the simplest case, rectangular or semicircular chicanes were installed over the whole height of the cavity at its walls.

It is therefore proposed that the region is a rectangle or a segment of a circle.

Furthermore, the given cross-section of the employed geometry of the cavities can widen in the height direction, in order for example to guarantee better mould removal in the case of injection moulding, or narrow in the height direction, in order for example to increase further the filling volume at a corresponding shaking frequency, without spilling over of the liquid occurring.

As a further solution to the problem, use may be made of the aforementioned cavity geometries which then transform upwards or downwards in the height direction into another cavity geometry. The transition can take place between one of the cavity geometries described here or can transform into a round, square or rectangular cavity geometry. A transition can also take place between a round, square or rectangular cavity geometry.

By way of example, it is therefore proposed that a further cross-section intersecting the side wall parallel to the bottom has a round, square or rectangular shape.

For certain applications, it may also be advantageous if at least one component changing the cross-section is introduced into the cavity through the bottom or through a cover.

In order to enable measurements through the bottom, it is proposed that the bottom be constituted by an optically transparent material.

It is advantageous if the microreactor comprises a plurality of cavities which are disposed particularly preferably in the form of an array.

Independently of the embodiments previously described and the advantages achievable therewith, it is advantageous and important to the invention if a microreactor—in particular a previously described reactor—comprises a special cover.

This cover preferably comprises a gas-permeable area, in order that, especially in the case of an array, each individual cavity is sealed against solids and liquids from the surroundings. At the same time, it is advantageous if there is provided above each cavity an opening which is constituted in its shape and size, as well as the material closing it, such that evaporation from the reaction liquid is greatly reduced and a mass transfer from the surrounding gas phase into the liquid phase in the cavity and in the reverse direction is not adversely affected.

Furthermore, it is proposed that the cover should comprise a reclosable area. It is particularly preferable if the cover is constituted in one piece with the wall and/or the bottom, apart from a gas-permeable and/or reclosable area.

It is advantageous if the cover comprises a sandwich material made from a firm, a flexible and/or a gas-permeable material. One embodiment makes provision such that the cover comprises a stable frame with a seal.

The cover can be fixed in place by pretensioning against the wall and it can be fixed to the wall according to the Luer principle. It is preferable here for the male part of a Luer lock to be provided on the cover and for the wall to form the female counter-part.

One variant makes provision such that the cover is connected to the wall by means of oblique planes displaceable against one another. This can be achieved for example by the fact that, for the detachment of the cover from the wall, a wedge can be inserted into a gap in order to detach the cover from the wall.

In order to lift off the cover, it is proposed that, in order to detach the cover, holes are disposed in the cover into which a gripper can engage. In particular, it is advantageous here if the gripper for detaching the cover comprises an arrangement for applying a mechanical or pneumatic counter-pressure. For example, for the detachment of an anchored cover, holes can be provided in openings, through which the pins or hollow needles of a gripping arm can apply a mechanical or pneumatic pressure to the cavity in order to detach the cover from the reaction vessel arrangement.

In order to fix the cover, it is proposed that the cover is glued to the wall. Furthermore, the cover can be fixed in a latching manner to the wall or it can comprise a device for generating an underpressure in the cavity.

It is advantageous if the cover enables a supply and removal of reaction participants and sampling without interruption of the shaking process.

An example of embodiment makes provision such that the microreactor forms a part of a microreactor array with a plurality of identical cavities and it preferably comprises a shaking device.

The drawing shows measurement results and variants of embodiment in respect of microreactors, reactor arrays and various covers for reactors and reactor arrays.

Figure 4:
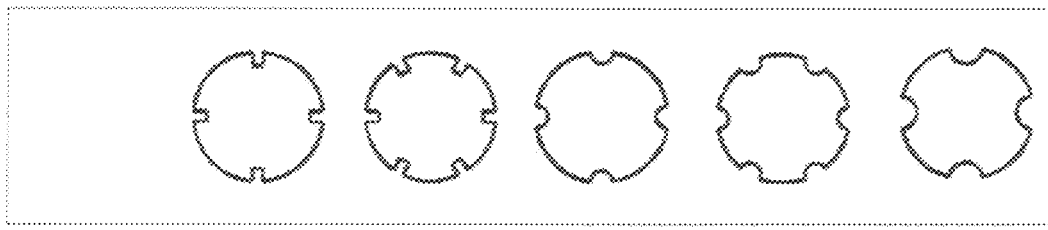
Figure 5:
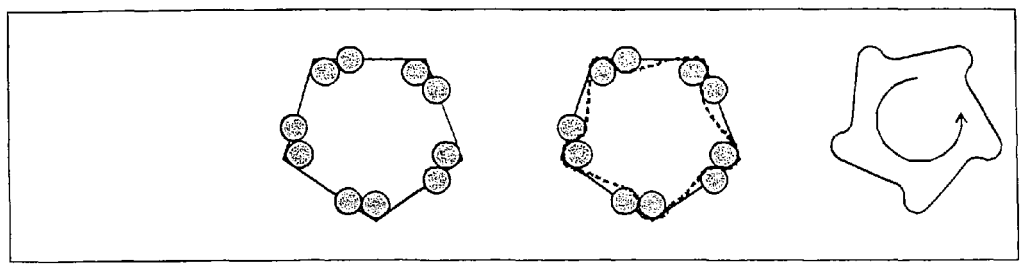
Figure 6:
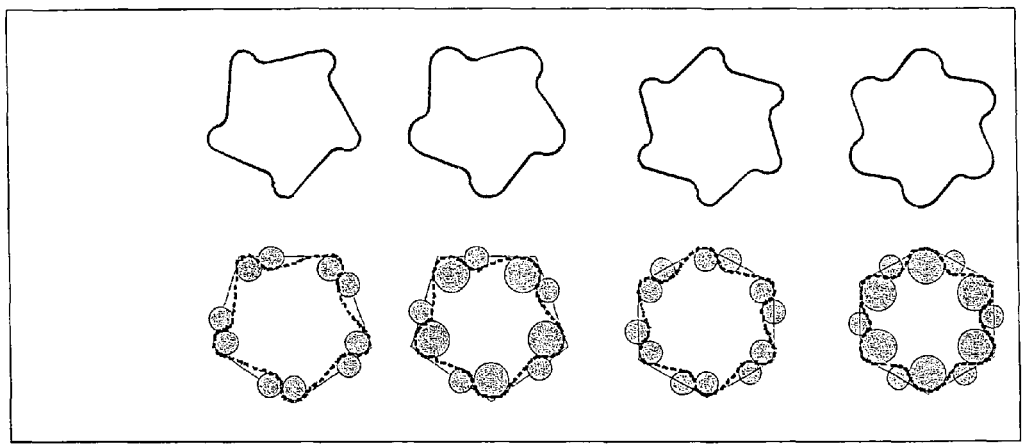
Figure 7:
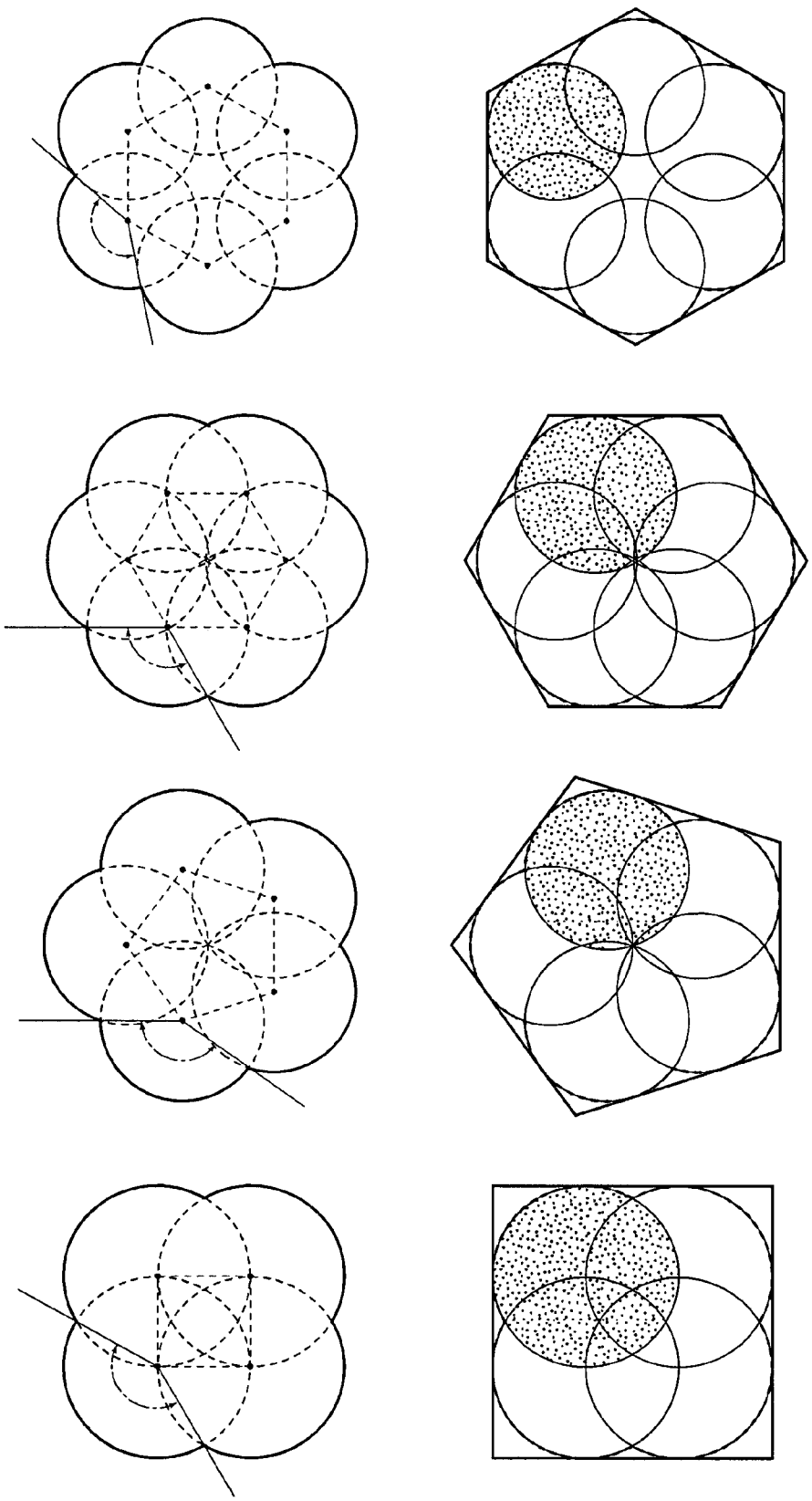
Figure 8:
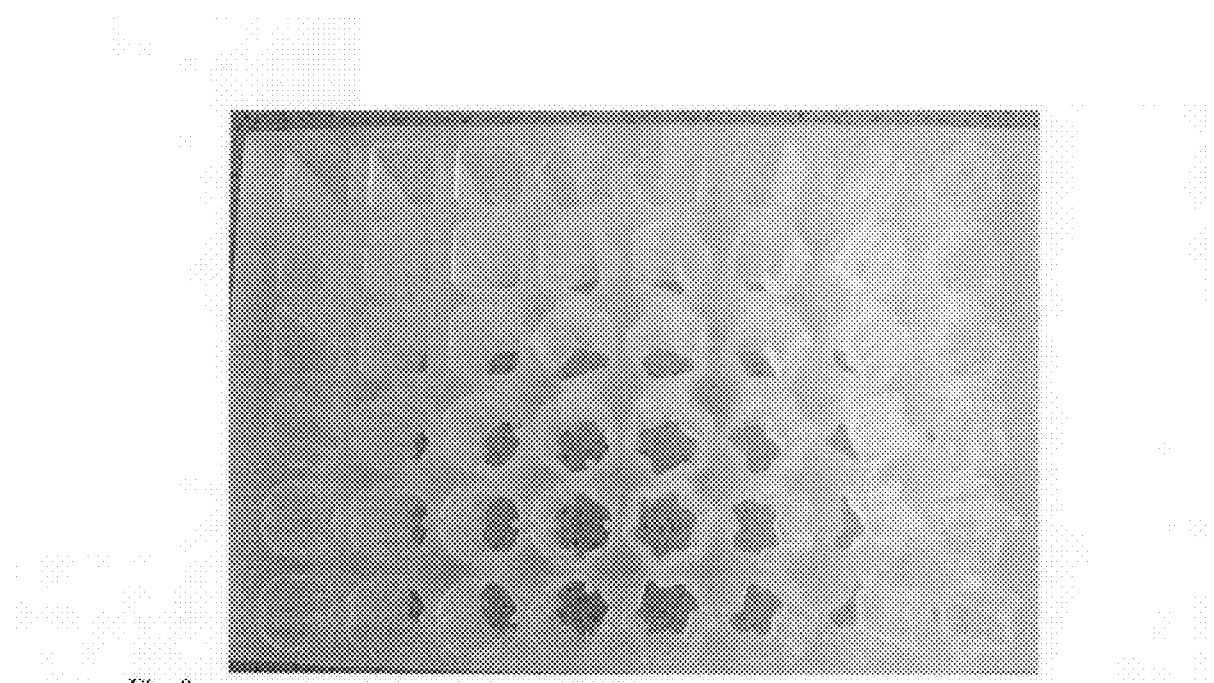
Figure 9:
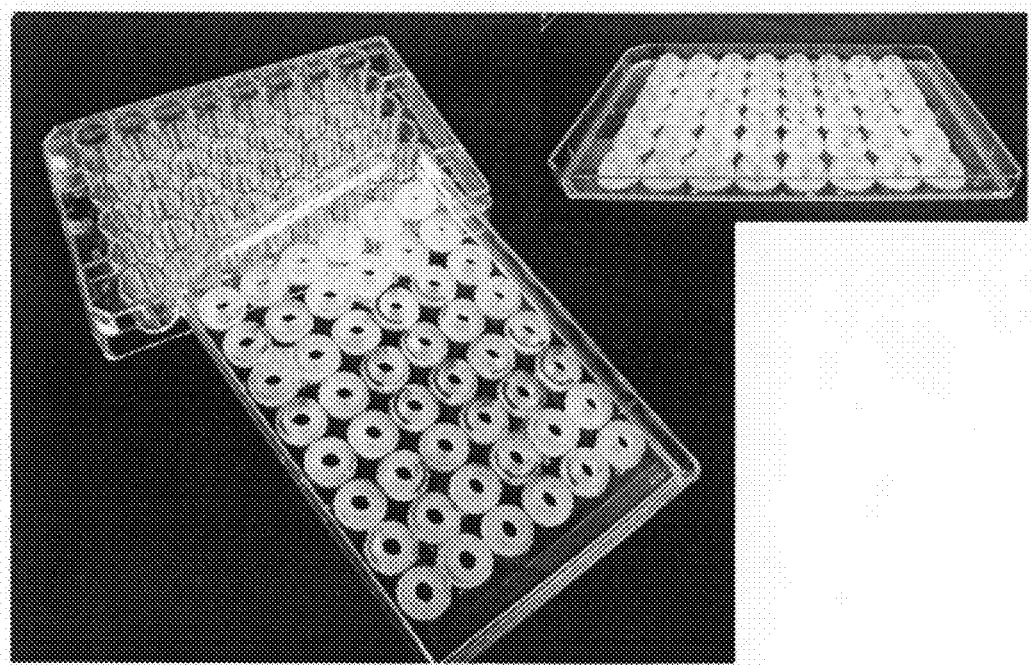
Figure 10:
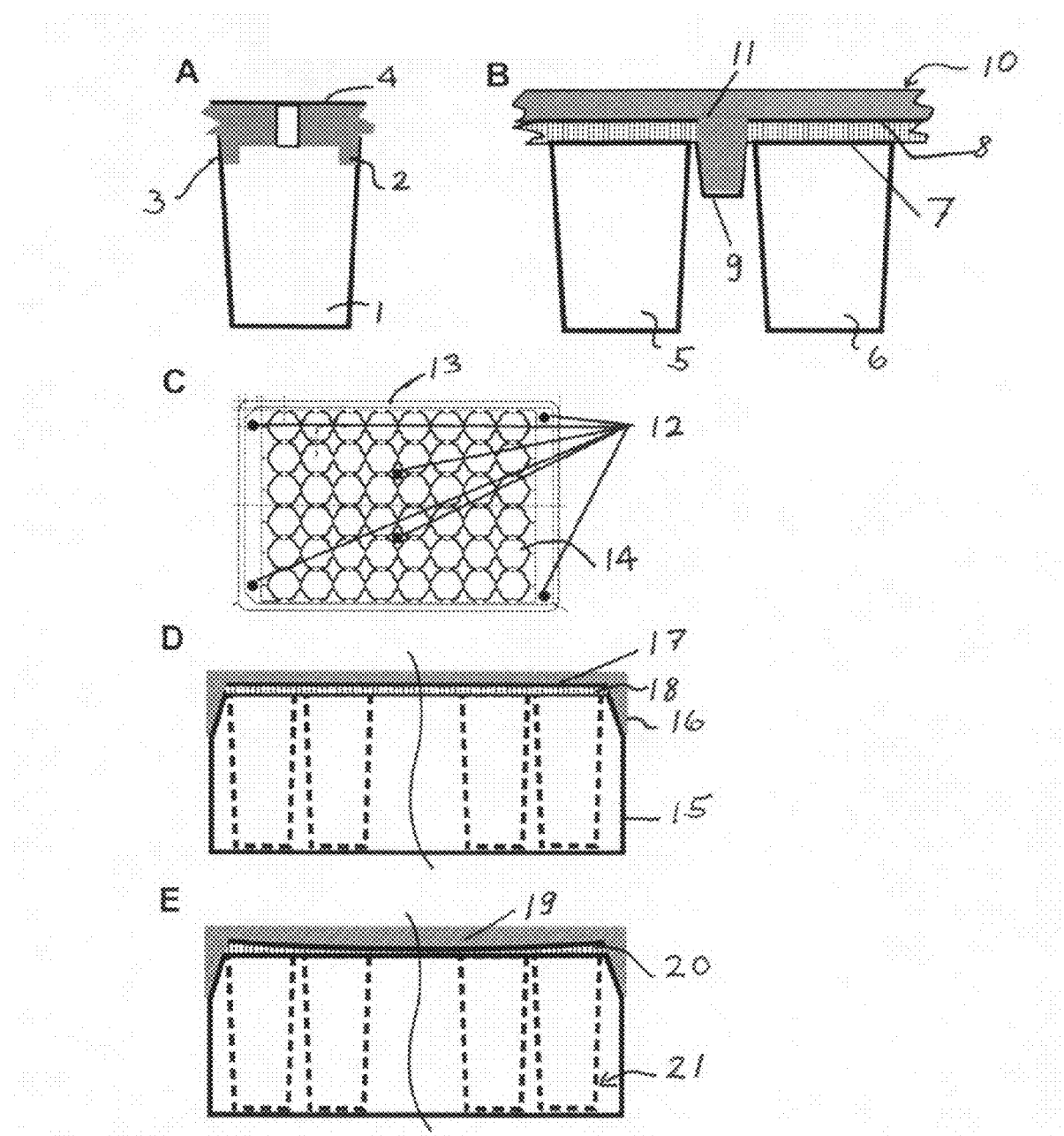
Figure 11:
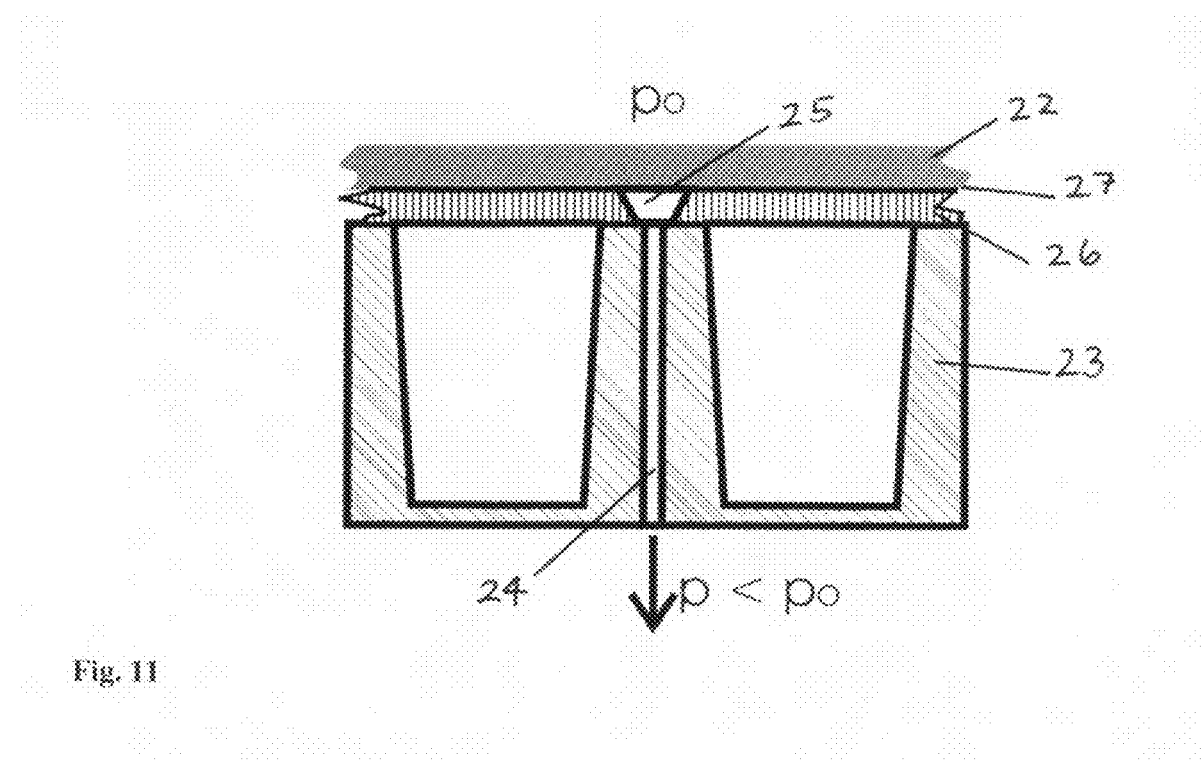
Figure 12:
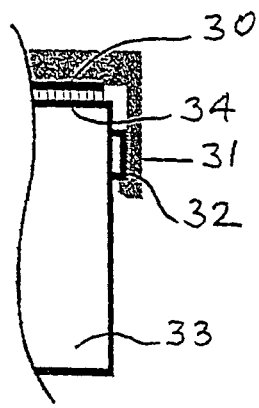
Figure 12:
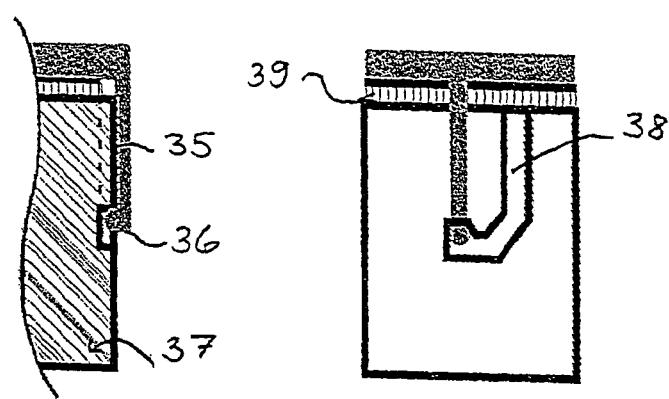
Figure 12:
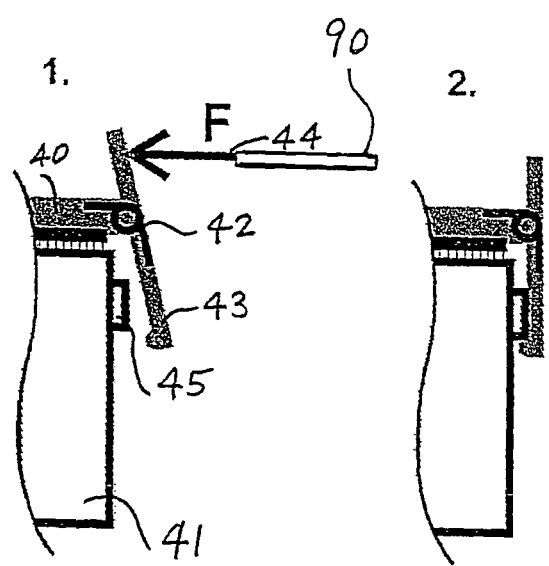
Figure 13:
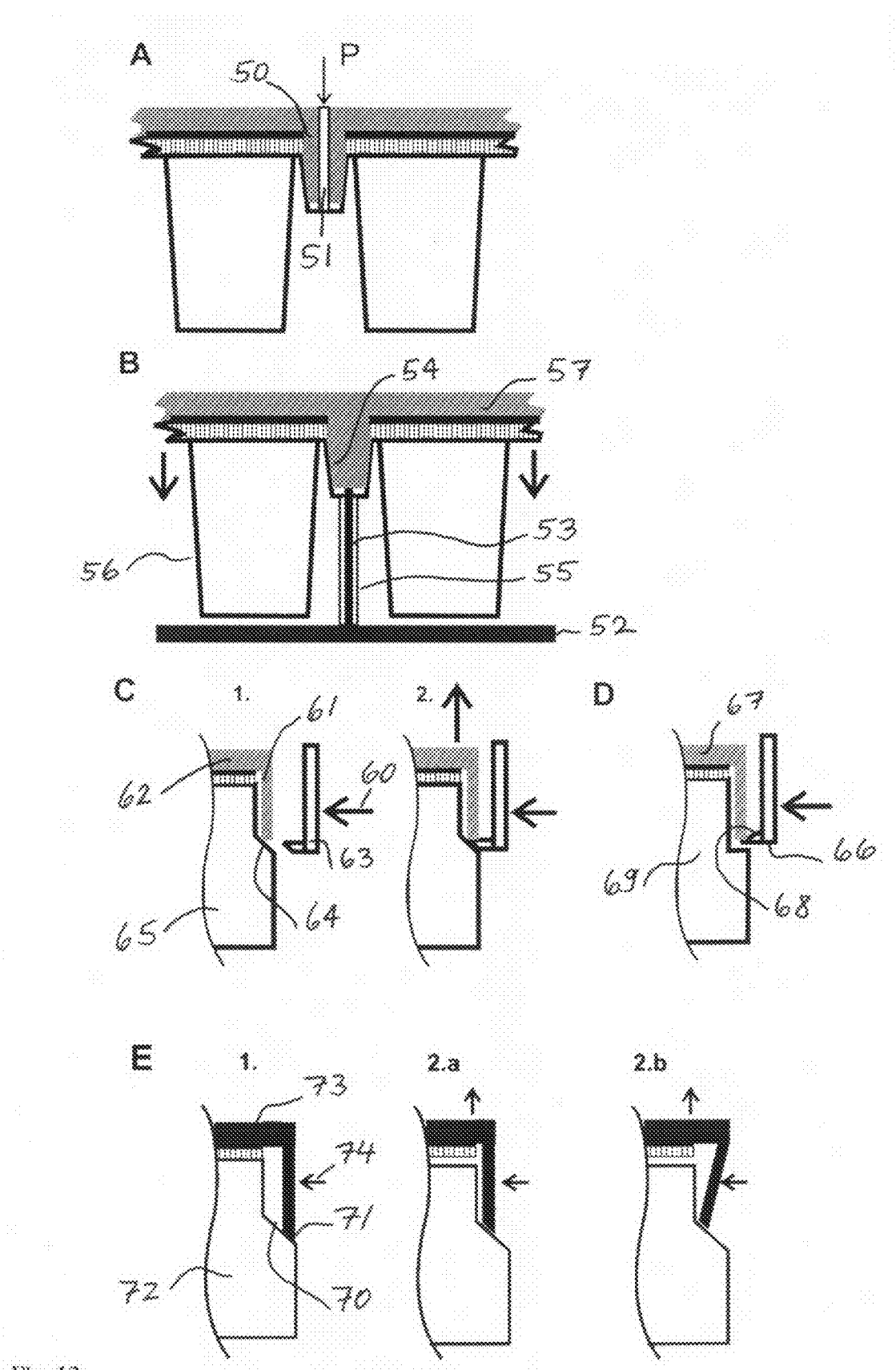
Figure 14:
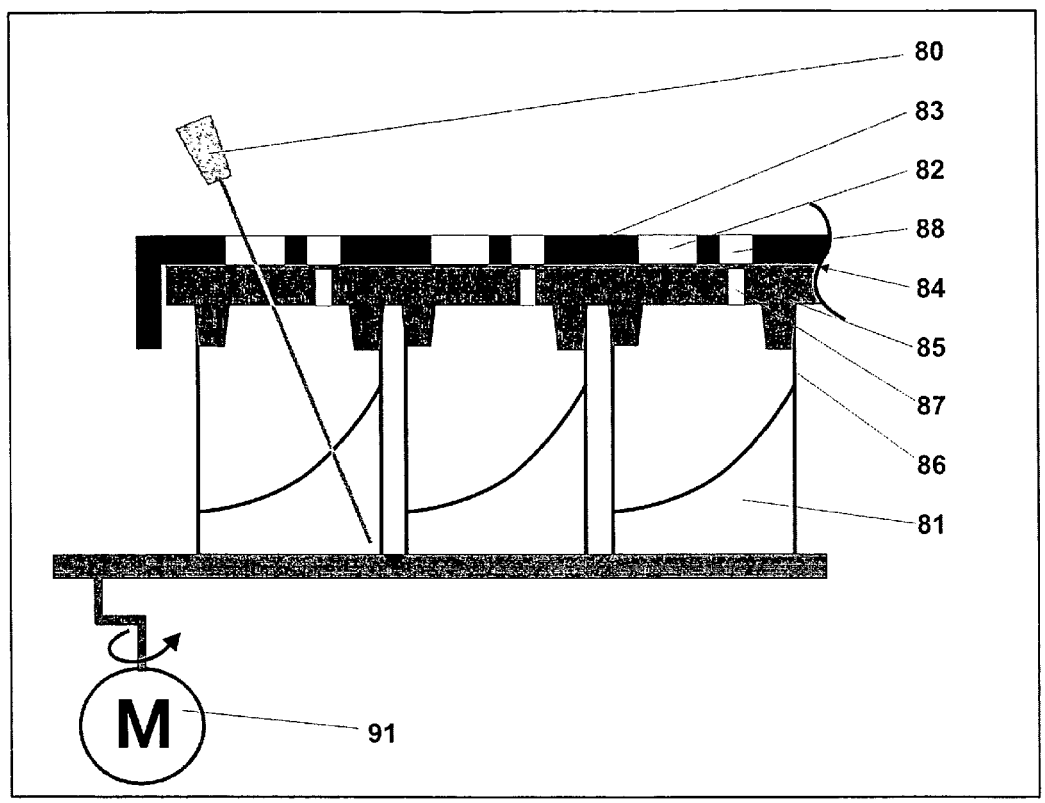
Figure 15:
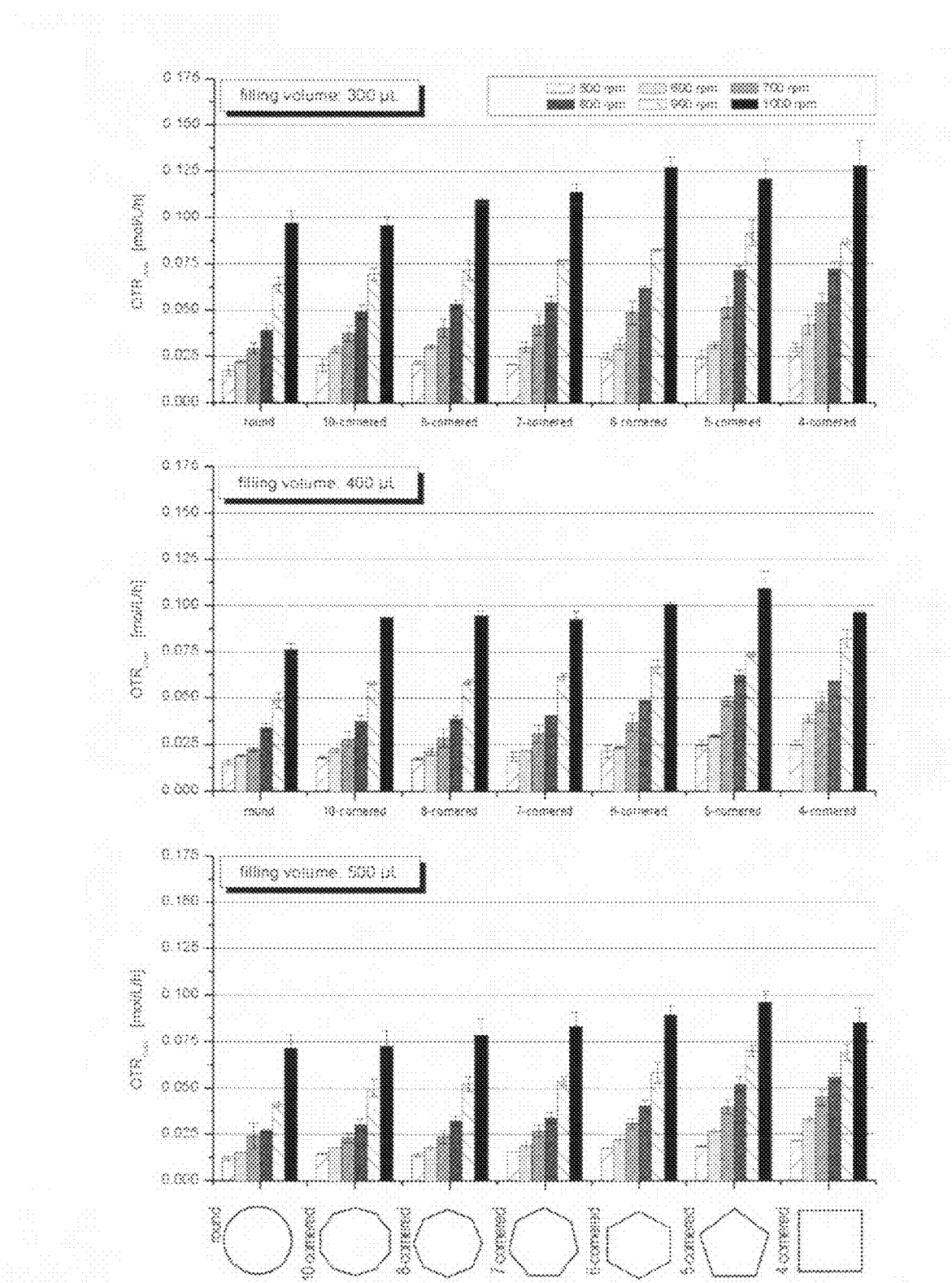
Figure 16:
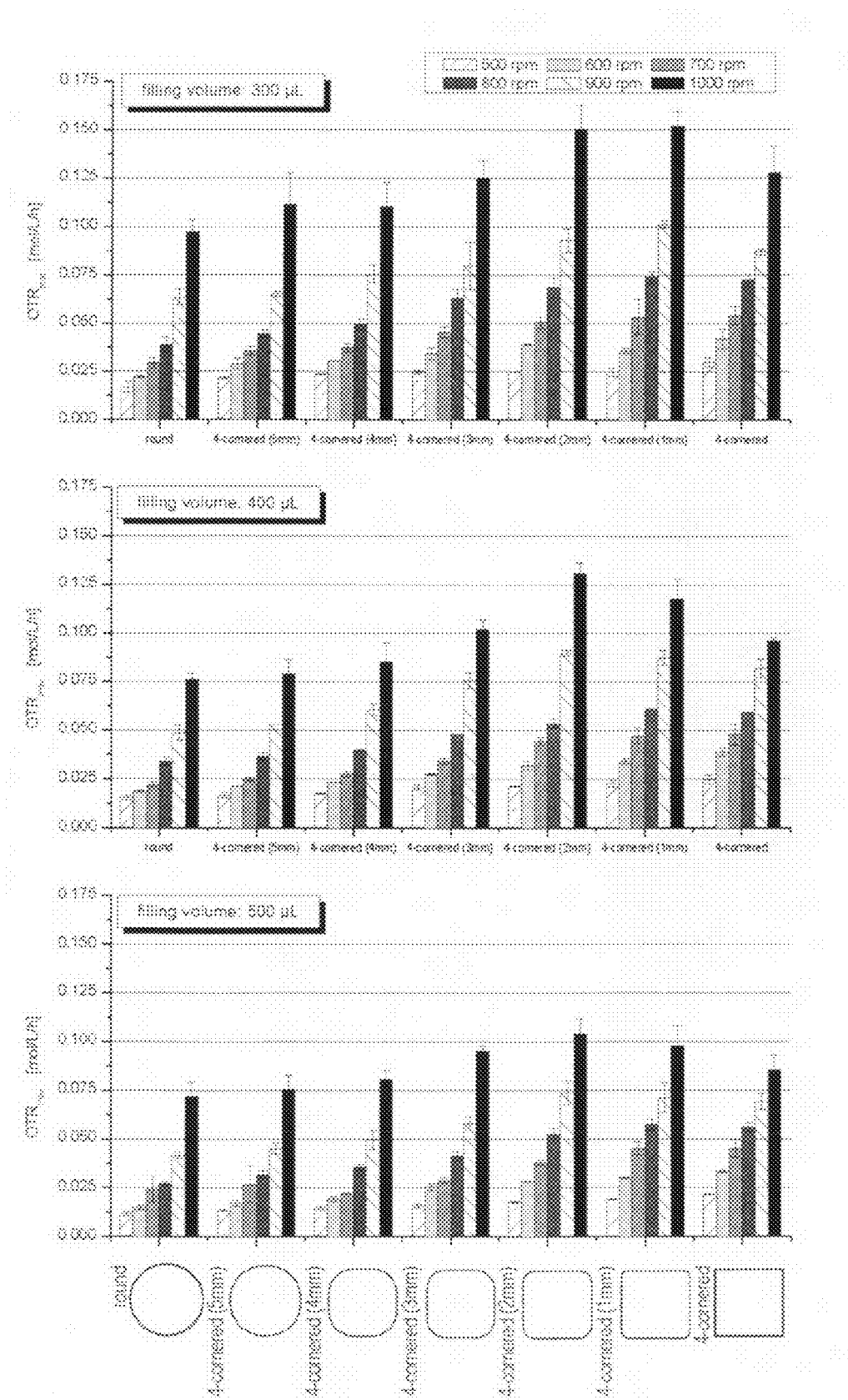
Figure 17A:
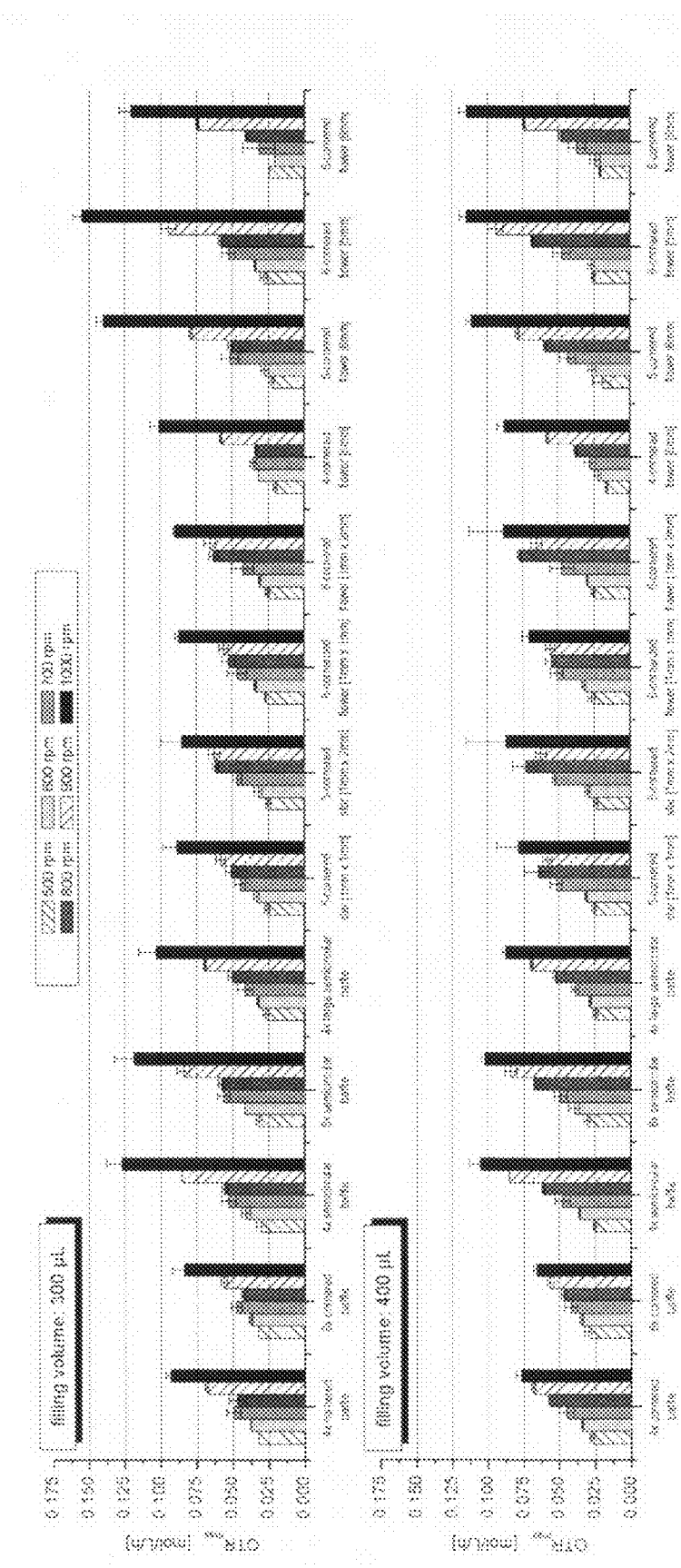
Figure 17:
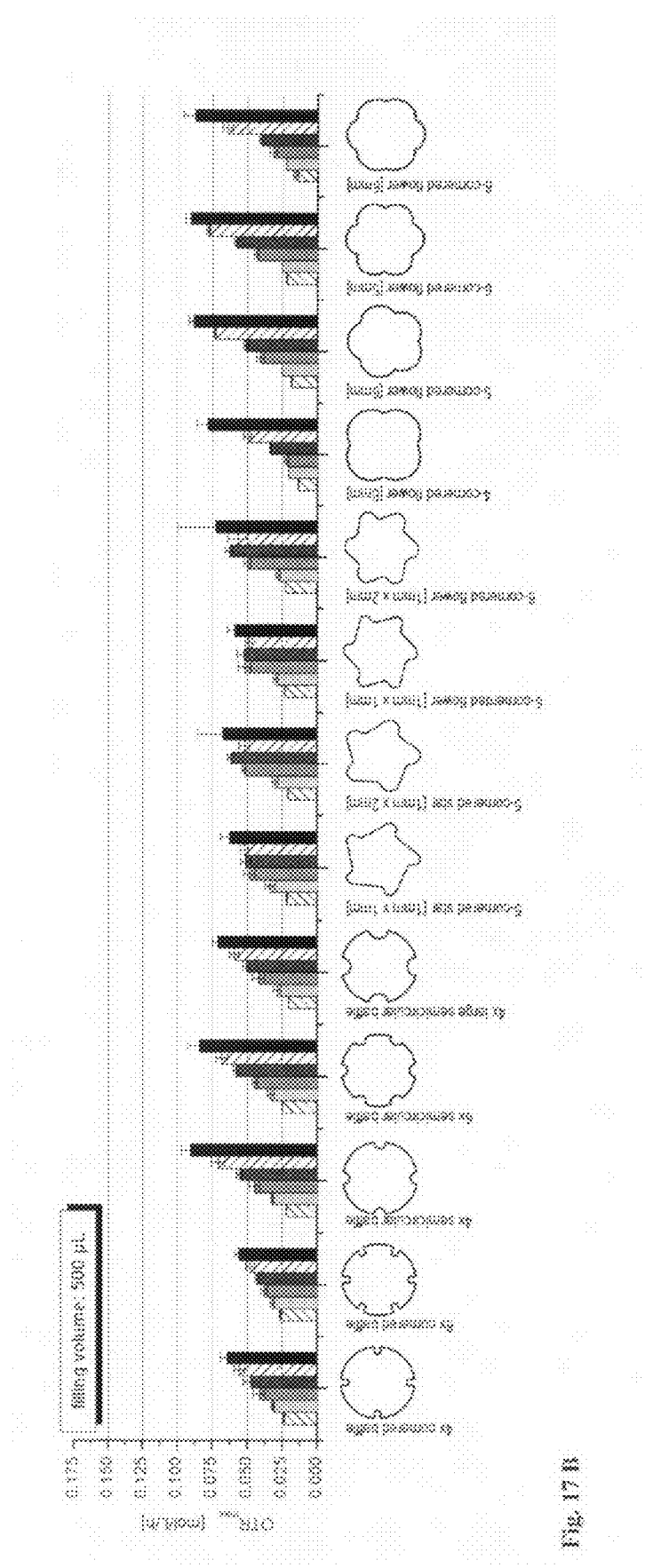
Figure 18:
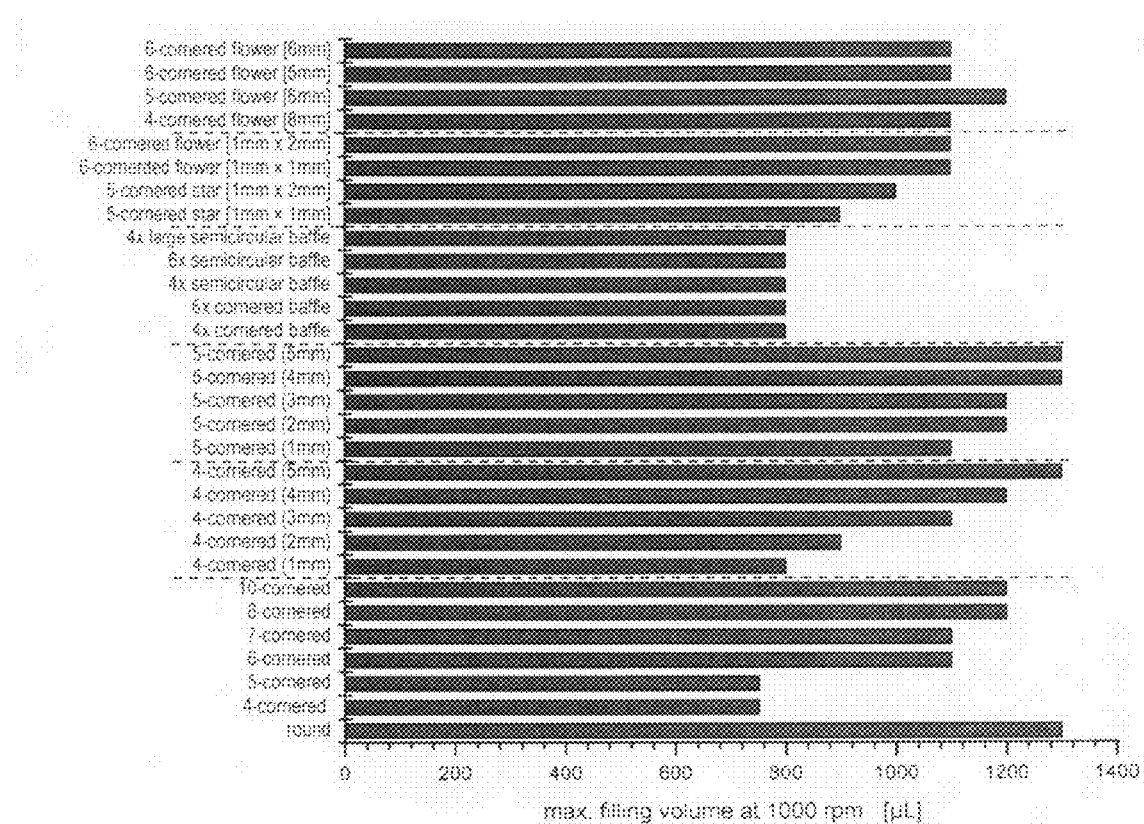
Figure 19:
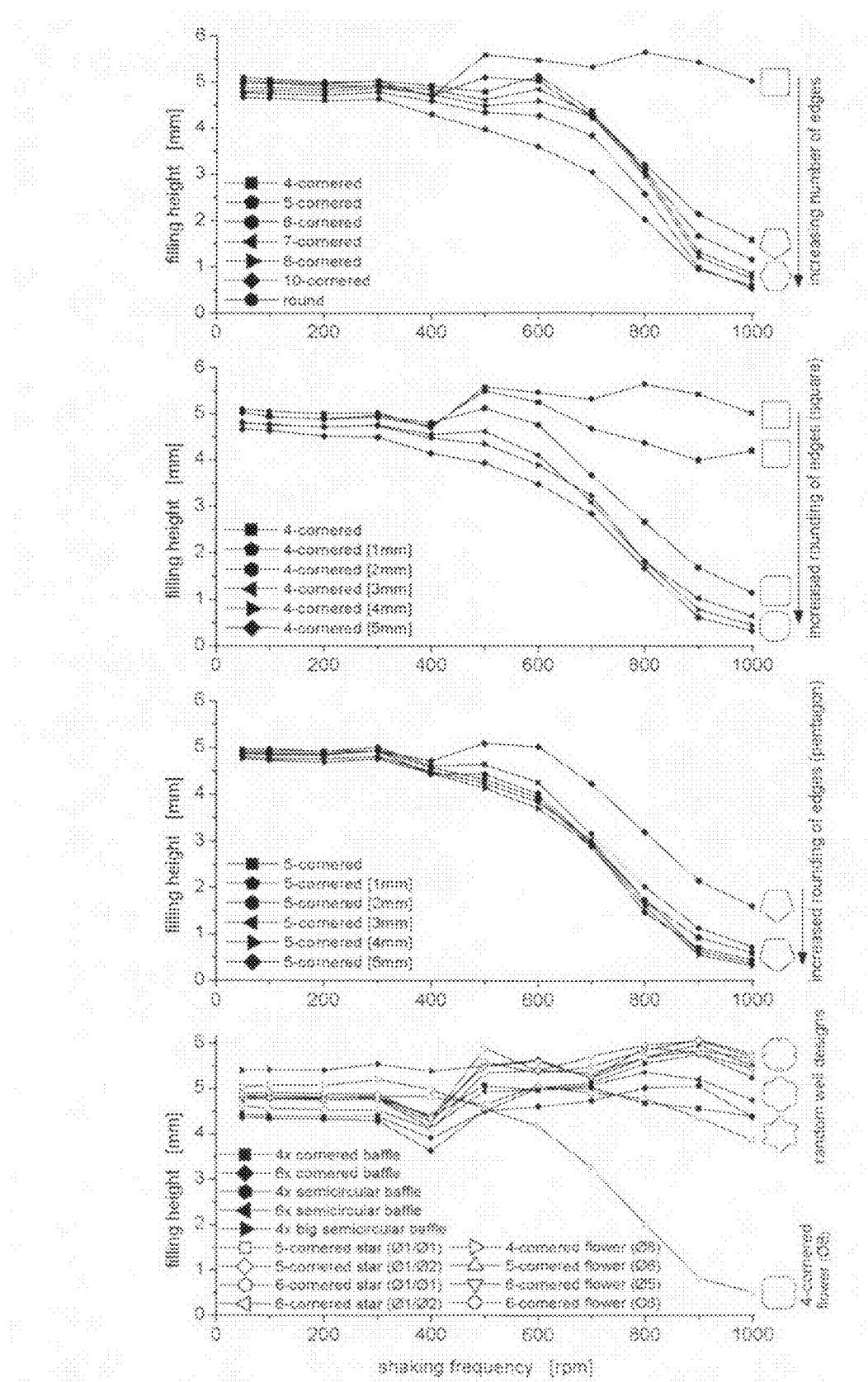

FIG. 4 shows diagrammatic representations of cavities with rectangular and semicircular flow disrupters, FIG. 5 shows diagrammatically the construction of a pentagonal base area with asymmetric semicircular chicanes, FIG. 6 shows diagrammatically pentagonal and hexagonal base areas with asymmetric semicircular chicanes, FIG. 7 shows diagrammatically square, pentagonal and hexagonal base areas with rounded corner chicanes and apex chicanes, FIG. 8 shows a photograph of various microreactor geometries arranged as an array, FIG. 9 shows a photograph of the prototypes of the cover with the Luer principle for microreactor arrays, FIG. 10 shows diagrammatic representations to explain the Luer principle, FIG. 11 shows diagrammatically an arrangement for holding the cover to a microreactor array by underpressure, FIG. 12 shows diagrammatically the representation of hooks for holding the cover to a microreactor array, FIG. 13 shows diagrammatically possibilities for detaching the cover from the microreactor array, FIG. 14 shows diagrammatically a multifunctional cover placed onto a microreactor array, FIG. 15 shows graphic representations of measurement results for the maximum oxygen transfer rate in different exemplary geometries, FIG. 16 shows graphic representations of measurement results for the maximum oxygen transfer rate in further created exemplary geometries, FIG. 17 shows, graphically represented, measurement results for the maximum oxygen transfer rate in the case of exemplary geometries with chicanes, FIG. 18 shows measurement results for the maximum filling volume in created exemplary geometries and FIG. 19 shows measurement results for the measurable filling height in a cavity in created exemplary geometries in the presence of an orbital shaking motion.

Figure 1:
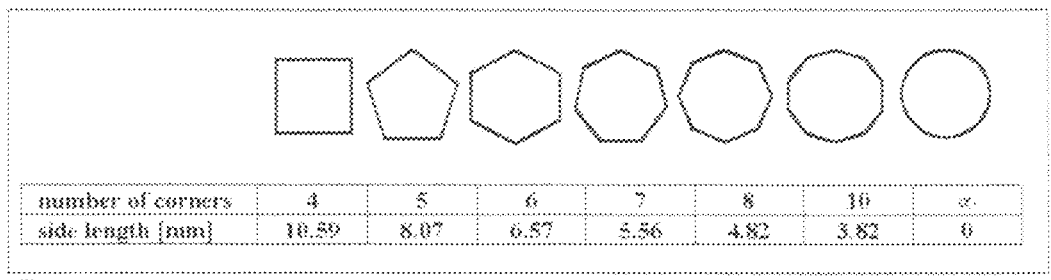
FIG. 1 shows variations of the number of corners of a cavity.

FIG. 1 shows how the construction-relevant length of the base side of a polygon can be calculated for a given area—of 112.16 mm$^2$ in the present example—by the construction of a triangle between a base side and two adjacent radii of the polygon.

Figure 2:
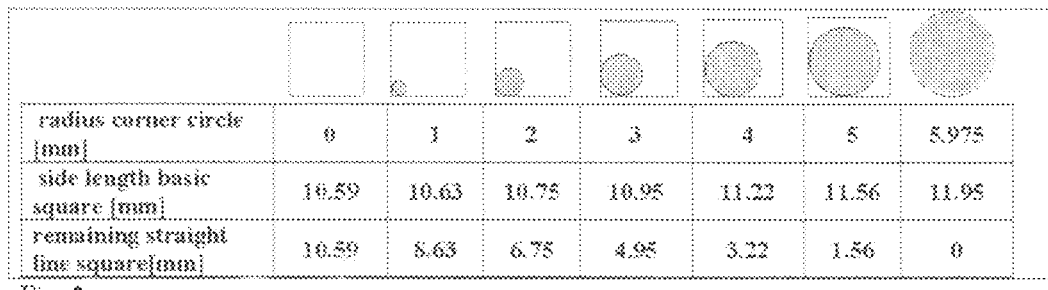
FIG. 2 shows variations of the formation of corners in a square cavity.

The approach at a variation shown in FIG. 2 proceeds from a square, wherein the transition to the circular base area takes place by the construction of circles with increasing radius in the corners of the square. The magnitudes of the radius of the corner circle and the remaining straight line of the initial square are of relevance for the construction. Their calculation takes place by the construction and calculation of a kite polygon with the centrepoint of the corner circle in the corner of the initial square.

Figure 3:
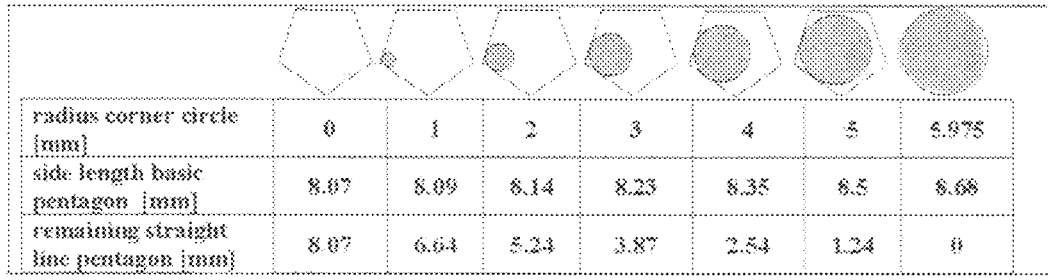
FIG. 3 shows variations of the formation of the corners in a pentagonal cavity.

The same procedure using the example of a pentagon as the initial shape is shown in FIG. 3.

FIG. 4 shows how an initially circular basic shape of a cavity can be modified, in that flow disrupters of different shape and size are introduced. The base area arising here cannot be readily calculated in many areas. In order to meet the stipulation of 112.16 mm$^2$, the area was measured after drawing with a CAD system and then scaled. As examples, rectangular and hemispherical chicanes were installed here over the whole height of the cavity at its walls. These are however only examples and both the shape of the chicanes and their extension over the height of the cavity can vary in different examples of embodiment.

FIGS. 5 to 7 show base area geometries which have emerged in the most diverse geometrical shapes from theoretical considerations of suitable transformations. In the case of all these basic shapes, circles of defined magnitude were introduced, the radius whereof was changed in 1 mm steps. The selection of the geometries resulting therefrom was made on the basis of a purely theoretical assessment of their influence on the flow in the cavity. Shapes with extremely strongly pronounced or very weakly pronounced flow disrupters are thus excluded from the consideration.

FIGS. 6 and 7 show base areas of flow disruptors which proceed from a pentagonal or hexagonal base area. Their construction is represented by way of example in FIGS. 6 and 7. The corners of these base areas have been rounded off, one or two millimeters having been adopted as the radius for the corner circles. A hemispherical chicane with a radius of 1 mm is disposed at each corner. This construction prescribes a direction of rotation for shaking for the cavities due to the lack of symmetry.

Further basic shapes of cavities are represented in FIG. 7. The corners are again rounded off proceeding from square, pentagonal, hexagonal or heptagonal basic shapes, the area between these corners in this case not being flat, but having a point extending inwards. These points form the chicanes in these cavities.

The array shown in FIG. 8 comprises different cavities and serves to investigate the performance function of different geometries.

The cover of a microreactor array created as a prototype shown in FIG. 9 closes each individual cavity tightly against the surroundings and has an opening above each cavity, said opening being constituted such that evaporation of the reaction liquid is greatly reduced and a mass transfer from the surrounding gas phase into the liquid in the cavity and in the reverse direction is not adversely affected.

Individual ones or all of the reactors of a microreactor array are constituted as Luer sleeves with respect to the cover formed with Luer cores. The embodiment of all the cavities as a Luer sleeves is advantageous, in order at the same time to achieve sealing of all the cavities with respect to the surroundings.

The Luer principle shown in FIG. 10 has proved to be very advantageous with this prototype. It is capable of closing the individual reaction spaces firmly and tightly with respect to the surroundings. For this purpose, cavity 1 is closed with a cover 2 which serves as a covering. Cover 2 has conical locating elements 3 which lie adjacent to the cavity wall and seal cover 2 to cavity 1. At its upper side, cover 2 has a gas-permeable film 4, which is glued onto the cover or is welded thereto. This film provides for the necessary gas exchange, reduced evaporation and the monoseptic operation. It is intended to make the components—microreactor array and fitting cover with occluding gas-permeable film—available to the user pre-sterilised.

A further embodiment is shown in FIG. 10B. A flexible sealing layer 7, on which a gas-permeable film 8 lies, is provided here on cavities 5, 6.

The microreactor array has a conical cavity in the body, which serves as a female Luer sleeve 9. A cover 10 for the microreactor array has a Luer core 11, which cooperates as the male part with sleeve 9 and holds the cover on the array.

Flexible layer 7 is applied over the cavities. It seals by means of suitable contact pressure of the cover which, held by the Luer connection, seals all the wells. The Luer sleeves can be provided for example between the individual wells and on the frame of the microreactor array. FIG. 10C shows a possible arrangement. In the latter, the possible positions are shown for Luer sleeves as fixing points 12 on microreactor array 13 for the sealing of cavities 14.

FIG. 10D shows how the Luer principle can be applied to the whole of the microreactor array. At least two opposite sides of array frame 15 are bevelled here. They thus serve as a Luer core for cover 16, which either forms a peripheral Luer sleeve or is put over the sides of array frame 15 only at the opposite-lying sides. Array cover 16 is thus constituted as a Luer sleeve and enters into a frictional connection with array frame 15. A gas-permeable film 17 and a flexible cover layer 18 are again provided between cover 16 and the microreactor array frame.

In order to guarantee a uniform or sufficient contact pressure of cover 19 on flexible layer 20 at every point of microreactor array 21, it is advantageous for cover 19 to bulge inwards, as is shown in FIG. 10E. This thus ensures a uniform stress distribution.

FIG. 11 shows a variant of embodiment, wherein cover 22 is sucked onto microreactor array 23 by vacuum or underpressure. For this purpose, suction is applied through a hole 24 in the body of microreactor array 23 and an underpressure is thus generated and the cover is pulled by a suction cup or a similar intermediate piece 25 to microreactor array 23. Flexible layer 26 with gas-permeable film 27 lying upon the latter is thus pressed onto the cavities in order to seal the latter. The pressing and sealing is active for as long as the vacuum is pulling, i.e. as long as the underpressure is generated. This connection can therefore easily be detached. Suction knobs 25 and holes 24 can be distributed arbitrarily on the array depending on the case of application.

FIG. 12A shows how cover 30 is fixed to the plate geometry by means of a barbed hook 31. In the example of embodiment, barbed hook 31 hooks onto a member 32. It is merely necessary here for cover 30 with its barbed hook 31 to be pushed onto microreactor array 33 from above or from the side. In the closed state, cover 30 is held so close to microreactor array 33 that it presses flexible layer 34 onto the cavities (not shown) and thus seals the latter.

FIG. 12B shows a variant, in which barbed hook 35 hooks into a groove 36 in microreactor array 37.

In order subsequently to detach cover 30 again, it is advantageous for barbed hook 35 of cover 30 to be guided in a guide groove 38. In the end position of guide groove 38, barbed hook 35 is held by the spring tension of flexible layer 39. For the purpose of engaging into and out of the end position, an external force must be applied to cover 30 by means of a gripping arm of a pipette robot or manually, which easily overcomes the spring tension of flexible layer 38.

FIG. 12D shows an alternative solution for fixing cover 40 on microreactor array 41 by the application of a spring tension by means of spring 42 on barbed hook 43. Only by the application of an external force 44 by means of a gripper 90, for example a gripping arm of a pipette robot or manually can the tension of spring 42 be counteracted and barbed hook 43 be splayed apart. By moving cover 40 downwards and the subsequent release of spring 42, cover 40 can be placed on and the barbed hook engaged onto side member 45.

In some applications, it may be necessary for the cover to be detached again from the microreactor array. This possibility should also be provided for by simple means without major accessories, apart from a simple liquid handling system with grippers (standard pipette robot). One possibility in this regard is shown in FIG. 13. On the one hand, it is possible to detach the Luer connection by means of an overpressure in the interior of the Luer sleeve, as shown in FIG. 13A. The overpressure can be applied by means of a compressed-air line through the hole in the Luer core, said compressed-air line being fitted on the gripping arm of a pipette robot. For this purpose, a compressed-air line 51 must be led to each Luer core 50.

FIG. 13B shows how pins 53 are provided on a plate 52, said pins pressing Luer cores 54 loose from beneath. The plate is simply placed on pins 53 and pins 53, guided through holes 55 in microreactor array base body 56, push cover 57 against Luer cores 54.

If a plurality of Luer connections or other frictional connections are used over the microreactor array in order to fix the cover, it is advantageous if a force does not have to be exerted in a targeted manner at each individual connection. The construction represented in FIG. 13C shows a solution for this. Here, force 60 is applied only to external frame 61 of cover 62, wherein bevelled shoe 63 are guided as fingers of a gripping arm horizontally beneath cover 62. At bevelled wall 64 of microreactor array 65, there is finally a deflection of force 60 into the vertical, whereby shoe 63 passes beneath cover 62 and raises the latter. The movement of shoes 63 forces a relative motion of microreactor array 65 with respect to cover 62 and thus detaches it.

A simple modification of this principle is shown in FIG. 13D. Here, shoe 66 is bevelled upwardly. Cover 67 passes upwards over bevel 68, microreactor array 69 remaining in its fixed position.

A further release mechanism is represented in FIG. 13E. This release mechanism manages without a special bevelled shoe at the fingers of a gripping arm. By providing two mirror-inverted bevels 70 and 71 on microreactor array 72 and cover 73, it is possible by applying a horizontal force 74 on the cover, which is formed partially flexible at this side face, to bring about a deflection of force 74 into the vertical according to the principle described above.

It is becoming increasingly necessary not only to acquire online information from the reactor sets of a microreactor array through the appropriate use of sensors in or on the reactors, but also to verify the reaction states changing over time with further offline analysis or to gain further insights. It is therefore important to obtain sample material from the individual reactors also during the conduct of the reaction and to continue the reactions thereafter in an uninfluenced manner. It may also be necessary to supply or remove liquid or solid substances to or from the reaction mixture. It is therefore necessary to obtain a reversible access to the reaction vessel. For this reason, in addition to the opening in the cover for the gas-permeable layer, an opening should also be provided for sampling and/or the supply and removal of substrates/reaction participants.

The use of a septum material of silicon or another flexible polymer, which closes again by itself on account of its material properties, is provided for this. Finally, the septum should be pierceable with a cannula 80, a pipette or a pipette needle in order to pipette sample material 81 into or out of the cavity interior. After withdrawal of cannula 80 and reclosure of the septum, the reaction should continue to proceed unaffected. Sterile sampling is extraordinarily important especially with cellular applications, in order to not permit any contamination of the usually monoseptic culture management.

It is advantageous, especially in the case of very rapid reactions and fermentations, to carry out the sampling or the intervention into the process without interrupting the shaking, in order not to limit the mass transport. For this, provision is made to carry out the shaking process with a diameter which is so small as to permit, even during the shaking process, penetration through a septum into the reaction space and the taking of a sample or the supply or removal of substrates. Shaking diameters of 1 to 5 mm are advantageous here. Moreover, it must be ensured that the cannula for the sampling during the shaking motion is deformed at most in the elastic region or is mounted flexibly.

The arrangement shown in FIG. 14 comprises a shaking device 91 and a cannula 80, which is passed through an opening 82 in a rigid cover back 83 through a gas-permeable film 84 and a flexible cover layer 85 into a cavity 86 in order to remove reaction liquid from cavity 86 or to introduce the same into the cavity. For the mass transport between interior and exterior, holes 87 are provided in flexible cover layer 85, said holes being aligned with openings 88 in rigid cover back 83.

The enormous advantages of a modified geometry of the cavities of a microreactor array have been able to be demonstrated in extensive tests with several prototypes. On the one hand, it has been able to be shown that it is possible to achieve an enormous increase in the oxygen transfer rate into the reaction liquid, the level whereof represents a limiting factor especially for microbial fermentations in microtitre plates according to the prior art. It has also been able to be shown that the cavity geometries (circular or square) used according to the prior art in available microtitre plates or deep-well plates in no way represent the optimum for the oxygen input. FIGS. 15 to 17 show the maximum mass transfer rates (here oxygen transfer rate: OTR (oxygen transfer rate)) with various geometries and shaking speeds as well as different working volumes (shaking diameter in each case 3 mm orbit). It can also be deduced from these measurement data that the cavity shape described in patent specification U.S. Pat. No. 5,225,164 cannot be optimum either, because the combination of the square basic shape with angular flow disrupters does not give reason to expect maximum oxygen input, but on the contrary a marked drop formation can be observed.

Spilling over and the formation of drops during an orbital shaking motion were investigated in a further series of tests. An investigation was made for each of the created embodiments to establish the maximum filling volume with a shaking speed of 1000 revs/min and a shaking diameter of 3 mm in a 20 mm high prototype microtitre plate (FIG. 18).

It can be shown that an advantageous behaviour of the liquid arises if the protrusions or indentations acting as flow breakers are only small, or have moderate gradients.

Apart from these two advantages of the invention, an increased mass transfer with at the same time a low tendency to drop formation or spilling over of the reaction liquid, a further important advantage of the invention lies in the prevention of the bottom of the cavity running dry. In order to investigate this property, the layer thickness of the liquid present at the bottom of a well during the rotation of the shaker was calculated back via the fluorescence intensity of a fluorescein solution. The results described in FIG. 19 show that the more pronounced the corners and edges, the more the liquid is prevented from expanding over the cavity walls and thus from escaping from the bottom.

The simultaneous consideration of the three described test series (oxygen input, maximum filling volume, bottom running dry) reveals that the invention fundamentally improves the concept of the microtitre plate compared to the prior art, especially for its application as a cell cultivation system. Due to the fact that a much higher oxygen input can be achieved, with at the same time sufficiently homogeneous hydrodynamics without drop and splash formation, a largely unlimited fermentation of microorganisms and higher cells (plant, animal and human cells) is possible. As a result of preventing the bottom of the cavity from running dry, a sufficiently high liquid column remains at the bottom of the cavity even at high shaking speeds. The liquid is thus much more readily accessible for measurement at the bottom of the cavity. Sensors installed here do not run the risk of losing contact with the reaction mixture.

The novel design of the cover of the microtitre plate overcomes a serious drawback which normally arises with cultivation in microtitre plates. The loss of liquid from the cavity arising in particular at higher cultivation temperatures is markedly reduced. At the same time, a sufficient gas exchange between the surroundings and the reaction volume is enabled. Each cavity remains accessible for sampling through a septum. As a result of the structure of the cover made from a dimensionally stable part and a flexible material for the covering as well as the possibility of easy detachment of the cover, the invention offers the possibility for installing the system in automated systems (pipette robot; gripping arm) without major additional equipment or special applicators.

The invention claimed is:

1. A microreactor comprising:
   a bottom;
   a side wall;
   an opening disposed opposite the bottom, wherein the bottom, the side wall and the opening form a cavity for receiving a liquid; and
   a cover sealing the cavity;
   wherein the cavity comprises a first cross-section disposed in a first plane intersecting the side wall and parallel to the bottom, the perimeter of the first cross section comprising at least four convex arcs, the at least four convex arcs comprising:
      a first convex arc disposed in the first plane, the first convex arc comprising a first segment of more than ninety degrees of a first imaginary circle having a first center disposed within the perimeter;
      a second convex arc disposed in the first plane, the second convex arc comprising a second segment of more than ninety degrees of a second imaginary circle having a second center disposed within the perimeter;
      a third convex arc disposed in the first plane, the third convex arc comprising a third segment of more than ninety degrees of a third imaginary circle having a third center disposed within the perimeter; and
      a fourth convex arc disposed in the first plane, the fourth convex arc comprising a first segment of more than ninety degrees of a fourth imaginary circle having a fourth center disposed within the perimeter;
      wherein the first center, the second center, the third center and the fourth center are each located at a different point in the first plane, and the first center, the second center, the third center and the fourth center form an imaginary polygon.

2. The microreactor according to claim 1, wherein the first cross-section comprises more than four corners.

3. The microreactor according to claim 1, wherein the first cross-section comprises corners with a radius of more than 0.5 mm.

4. The microreactor according to claim 1, wherein a second cross-section intersecting the side wall parallel to the bottom has a round, square or rectangular shape.

5. The microreactor according to claim 1, further comprising at least one component protruding from the bottom of the cavity or protruding from the cover into the cavity, the at least one component changing the first cross-section.

6. The microreactor according to claim 1, wherein the bottom is made from an optically transparent material which enables measurements through the bottom.

7. The microreactor according to claim 1, wherein the cavity comprises a plurality of cavities.

8. The microreactor according to claim 1, wherein the cover comprises a gas-permeable area.

9. The microreactor according to claim 1, wherein the cover comprises a reclosable area.

10. The microreactor according to claim 1, wherein the cover is in one piece with at least one of the side wall and the bottom, apart from at least one of a gas-permeable and a reclosable area.

11. The microreactor according to claim 1, wherein the cover comprises a sandwich material made from at least one of a firm, a flexible and a gas-permeable material.

12. The microreactor according to claim 1, wherein the cover comprises a stable frame with a seal.

13. The microreactor according to claim 1, wherein the cover can be fixed in place by pretensioning against the side wall.

14. The microreactor according to claim 1, wherein a male part of a lock is provided on the cover and the side wall forms a female counter-part.

15. The microreactor according to claim 1, wherein the cover is connected to the side wall by a plurality of oblique planes displaceable against one another.

16. The microreactor according to claim 1, further comprising a wedge inserted into a gap in order to detach the cover from the side wall.

17. The microreactor according to claim 1, wherein the cover has a plurality of holes disposed therein and the plurality of holes are engageable by a gripper for detaching the cover.

18. The microreactor according to claim 1, further comprising a gripper for detaching the cover, the gripper comprising an arrangement for applying at least one of a mechanical and a pneumatic counter-pressure.

19. The microreactor according to claim 1, further comprising a plurality of pins for applying from beneath a mechanical pressure required to detach the cover.

20. The microreactor according to claim 1, wherein the cover is glued to the side wall.

21. The microreactor according to claim 1, wherein the cover is fixed to the side wall in a latching manner.

22. The microreactor according to claim 1, further comprising a device for generating an underpressure through the microreactor wall to the microreactor for pulling the cover.

23. A microreactor array comprising a plurality of microreactors according to claim 1 comprising a plurality of identical cavities.

24. The microreactor according to claim 1, further comprising a shaking device.

* * * * *